(12) United States Patent  
Viola

(10) Patent No.: US 8,372,095 B2  
(45) Date of Patent: *Feb. 12, 2013

(54) ENDOSCOPIC SURGICAL CLIP

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,090

(22) Filed: Feb. 3, 2011

(65) Prior Publication Data

US 2011/0125171 A1    May 26, 2011

Related U.S. Application Data

(63) Continuation of application No. 10/421,151, filed on Apr. 22, 2003, now Pat. No. 7,896,896.

(60) Provisional application No. 60/374,623, filed on Apr. 22, 2002.

(51) Int. Cl.
  A61B 17/08  (2006.01)
  B42F 1/02   (2006.01)

(52) U.S. Cl. .......................... 606/158; 24/545

(58) Field of Classification Search ............ 606/141, 606/142, 148, 157, 158, 221; 24/456, 555, 24/563, 545
  See application file for complete search history.

(56) References Cited

U.S. PATENT DOCUMENTS

| 596,150 | A | 12/1897 | Fitch |
|---|---|---|---|
| 2,335,903 | A | 7/1942 | Beckett |
| 2,685,193 | A | 8/1950 | Marymont |
| 3,043,547 | A | 2/1960 | Reich |
| 3,032,039 | A | 5/1962 | Beaty |
| 3,056,408 | A | 10/1962 | Brown |
| 3,098,232 | A | 7/1963 | Brown |
| 3,363,628 | A | 1/1968 | Wood |
| 3,446,212 | A | 5/1969 | Le Roy |
| 3,463,156 | A | 8/1969 | McDermott |
| 3,535,746 | A | 10/1970 | Thomas, Jr. |
| 3,543,353 | A | 12/1970 | Meehan |
| 3,604,425 | A | 9/1971 | LeRoy |
| 3,631,707 | A | 1/1972 | Miller |
| 3,633,253 | A | 1/1972 | Ellis |
| 3,797,076 | A * | 3/1974 | Watkin ............ 24/562 |
| 3,822,441 | A | 7/1974 | Paxton |
| 3,840,943 | A | 10/1974 | Langwell |
| 3,882,854 | A | 5/1975 | Hulka et al. |
| 3,958,576 | A | 5/1976 | Komiya |
| 4,064,881 | A | 12/1977 | Meredith |
| 4,170,990 | A | 10/1979 | Baumgart et al. |
| 4,217,902 | A | 8/1980 | March |

(Continued)

FOREIGN PATENT DOCUMENTS

| DE | 2730691 | 1/1978 |
|---|---|---|
| DE | 4015562 | 11/1991 |

(Continued)

OTHER PUBLICATIONS

European Search Report for European Patent Appln. No. 11 25 0568 dated Aug. 4, 2011. (3 pages).

European Search Report for EP 03721818.7-1265 date of completion is May 29, 2009 (3 pages).

Primary Examiner — Tuan V Nguyen

(57) ABSTRACT

A surgical spring clip is provided for use in minimally invasive surgical procedures. The clip has a flat planar plate shape having pair of arms connected by a base, all generally positioned within a single plane. The arms are elongate linear cantilevered beams extending beyond the base and are biased to a first or closed position generally within the plane. The base and arms define a slot for the positioning of and receiving a vessel and occluding the flow therethrough.

14 Claims, 2 Drawing Sheets

U.S. PATENT DOCUMENTS

| | | | |
|---|---|---|---|
| 4,247,415 A | 1/1981 | Kimura et al. | |
| 4,274,415 A | 6/1981 | Kanamoto et al. | |
| 4,317,451 A | 3/1982 | Cerwin et al. | |
| 4,396,139 A | 8/1983 | Hall et al. | |
| 4,402,445 A | 9/1983 | Green | |
| 4,418,694 A | 12/1983 | Beroff et al. | |
| 4,433,689 A | 2/1984 | von Zeppelin | |
| 4,444,187 A | 4/1984 | Perlin | |
| 4,476,865 A | 10/1984 | Failla et al. | |
| 4,478,219 A | 10/1984 | Rozario et al. | |
| 4,484,581 A | 11/1984 | Martin et al. | |
| 4,485,816 A | 12/1984 | Krumme | |
| 4,492,232 A | 1/1985 | Green | |
| 4,506,670 A | 3/1985 | Crossley | |
| 4,512,345 A | 4/1985 | Green | |
| 4,513,746 A | 4/1985 | Aranyi et al. | |
| 4,527,562 A | 7/1985 | Mericle | |
| 4,534,350 A | 8/1985 | Golden et al. | |
| 4,534,352 A | 8/1985 | Korthoff | |
| 4,579,118 A | 4/1986 | Failla | |
| 4,590,937 A | 5/1986 | Deniega | |
| 4,607,638 A | 8/1986 | Crainich | |
| 4,610,250 A | 9/1986 | Green | |
| 4,612,932 A | 9/1986 | Caspar et al. | |
| 4,616,651 A | 10/1986 | Golden | |
| 4,620,541 A | 11/1986 | Gertzman et al. | |
| 4,638,804 A | 1/1987 | Jewusiak | |
| 4,646,741 A | 3/1987 | Smith | |
| 4,658,822 A | 4/1987 | Kees, Jr. | |
| 4,660,558 A | 4/1987 | Kees, Jr. | |
| 4,667,674 A | 5/1987 | Korthoff et al. | |
| 4,671,278 A | 6/1987 | Chin | |
| 4,696,396 A | 9/1987 | Samuels | |
| 4,702,247 A | 10/1987 | Blake et al. | |
| 4,741,337 A | 5/1988 | Smith et al. | |
| 4,765,335 A | 8/1988 | Schmidt et al. | |
| 4,777,949 A | 10/1988 | Perlin | |
| 4,777,950 A | 10/1988 | Kees, Jr. | |
| 4,791,707 A | 12/1988 | Tucker | |
| 4,796,625 A | 1/1989 | Kees, Jr. | |
| 4,796,627 A | 1/1989 | Tucker | |
| 4,799,481 A | 1/1989 | Transue et al. | |
| 4,805,617 A | 2/1989 | Bedi et al. | |
| 4,805,618 A | 2/1989 | Ueda et al. | |
| 4,822,348 A | 4/1989 | Casey | |
| 4,834,096 A | 5/1989 | Oh et al. | |
| 4,844,066 A | 7/1989 | Stein | |
| 4,932,960 A | 6/1990 | Green et al. | |
| 4,950,258 A | 8/1990 | Kawai et al. | |
| 4,957,500 A | 9/1990 | Liang et al. | |
| 4,961,743 A | 10/1990 | Kees, Jr. et al. | |
| 4,966,603 A | 10/1990 | Focelle et al. | |
| 4,972,949 A | 11/1990 | Peiffer | |
| 4,976,722 A | 12/1990 | Failla | |
| 4,983,176 A | 1/1991 | Cushman et al. | |
| 5,002,552 A | 3/1991 | Casey | |
| 5,002,563 A | 3/1991 | Pyka et al. | |
| 5,010,629 A | 4/1991 | Hirzel | |
| 5,035,692 A | 7/1991 | Lyon et al. | |
| 5,044,540 A | 9/1991 | Dulebohn | |
| 5,053,045 A | 10/1991 | Schmidt et al. | |
| 5,057,118 A | 10/1991 | Picha | |
| 5,062,846 A | 11/1991 | Oh et al. | |
| 5,062,848 A | 11/1991 | Frazee et al. | |
| 5,063,640 A | 11/1991 | Link | |
| 5,089,009 A | 2/1992 | Green | |
| 5,160,339 A | 11/1992 | Chen et al. | |
| 5,171,250 A | 12/1992 | Yoon | |
| 5,171,251 A | 12/1992 | Bregen et al. | |
| 5,201,746 A | 4/1993 | Shichman | |
| 5,207,692 A | 5/1993 | Kraus et al. | |
| 5,217,472 A | 6/1993 | Green et al. | |
| 5,217,473 A | 6/1993 | Yoon | |
| 5,219,353 A | 6/1993 | Garvey, III et al. | |
| 5,222,961 A | 6/1993 | Nakao et al. | |
| 5,234,449 A | 8/1993 | Bruker et al. | |
| 5,236,435 A | 8/1993 | Sewell, Jr. | |
| 5,242,456 A | 9/1993 | Nash et al. | |
| 5,257,713 A | 11/1993 | Green et al. | |
| 5,269,792 A | 12/1993 | Kovac et al. | |
| 5,282,812 A | 2/1994 | Suarez, Jr. | |
| 5,290,299 A | 3/1994 | Fain et al. | |
| 5,306,280 A | 4/1994 | Bregen et al. | |
| 5,312,426 A | 5/1994 | Segawa et al. | |
| 5,330,442 A | 7/1994 | Green et al. | |
| 5,342,373 A | 8/1994 | Stefanchik et al. | |
| 5,354,306 A | 10/1994 | Garvey, III et al. | |
| 5,366,458 A | 11/1994 | Korthoff et al. | |
| 5,366,459 A | 11/1994 | Yoon | |
| 5,366,479 A | 11/1994 | McGarry et al. | |
| 5,425,740 A | 6/1995 | Hutchinson, Jr. | |
| 5,441,509 A | 8/1995 | Vidal et al. | |
| 5,464,416 A | 11/1995 | Steckel | |
| 5,474,567 A | 12/1995 | Stefanchik et al. | |
| 5,487,746 A | 1/1996 | Yu et al. | |
| 5,495,644 A * | 3/1996 | Mesher et al. | 24/3.12 |
| 5,497,933 A | 3/1996 | DeFonzo et al. | |
| 5,501,693 A | 3/1996 | Gravener | |
| 5,520,701 A | 5/1996 | Lerch | |
| 5,540,704 A | 7/1996 | Gordon et al. | |
| 5,569,274 A | 10/1996 | Rapacki et al. | |
| 5,571,121 A | 11/1996 | Heifetz | |
| 5,593,414 A | 1/1997 | Shipp et al. | |
| 5,601,573 A | 2/1997 | Fogelberg et al. | |
| 5,601,574 A | 2/1997 | Stefanchik et al. | |
| 5,626,592 A | 5/1997 | Phillips et al. | |
| 5,632,753 A | 5/1997 | Loeser | |
| RE35,525 E | 6/1997 | Stefanchik et al. | |
| 5,634,932 A | 6/1997 | Schmidt | |
| 5,681,330 A | 10/1997 | Hughett et al. | |
| 5,683,405 A | 11/1997 | Yacoubian et al. | |
| 5,695,505 A | 12/1997 | Yoon | |
| 5,713,911 A | 2/1998 | Racenet et al. | |
| 5,725,542 A | 3/1998 | Yoon | |
| 5,741,277 A | 4/1998 | Gordon et al. | |
| 5,758,420 A | 6/1998 | Schmidt et al. | |
| 5,766,189 A | 6/1998 | Matsuno | |
| 5,769,857 A | 6/1998 | Reztzov et al. | |
| 5,827,306 A | 10/1998 | Yoon | |
| 5,833,700 A | 11/1998 | Fogelberg et al. | |
| 5,843,101 A | 12/1998 | Fry | |
| 5,849,019 A | 12/1998 | Yoon | |
| 5,858,018 A | 1/1999 | Shipp et al. | |
| 5,921,997 A | 7/1999 | Fogelberg et al. | |
| 5,941,890 A | 8/1999 | Voegele et al. | |
| 6,015,417 A | 1/2000 | Reynolds, Jr. | |
| 6,018,850 A * | 2/2000 | Lorber | 24/67.9 |
| 6,165,204 A | 12/2000 | Levinson et al. | |
| 6,179,850 B1 | 1/2001 | Goradia | |
| 6,193,732 B1 | 2/2001 | Frantzen et al. | |
| 6,193,733 B1 | 2/2001 | Adams | |
| 6,206,897 B1 | 3/2001 | Jamiolkowski et al. | |
| 6,210,418 B1 | 4/2001 | Storz et al. | |
| 6,226,843 B1 | 5/2001 | Crainich | |
| 6,241,740 B1 | 6/2001 | Davis | |
| 6,251,117 B1 | 6/2001 | Kringel et al. | |
| 6,273,903 B1 | 8/2001 | Wilk | |
| 6,346,112 B2 | 2/2002 | Adams | |
| 6,419,682 B1 | 7/2002 | Appleby et al. | |
| 6,468,285 B1 | 10/2002 | Hsu et al. | |
| 6,652,545 B2 | 11/2003 | Shipp et al. | |
| D508,397 S * | 8/2005 | Volk et al. | D8/395 |

FOREIGN PATENT DOCUMENTS

| | | |
|---|---|---|
| EP | 0346084 A1 | 12/1989 |
| EP | 0490411 A1 | 6/1992 |
| EP | 0592000 A2 | 4/1994 |
| EP | 0609612 A2 | 8/1994 |
| EP | 1 712 186 A2 | 10/2006 |
| GB | 2161206 A | 1/1986 |
| WO | WO88/01487 | 12/1988 |
| WO | WO88/01486 | 1/1989 |
| WO | WO95/05778 | 3/1995 |
| WO | WO 99/13780 | 3/1999 |
| WO | WO 02/087425 A | 11/2002 |

* cited by examiner

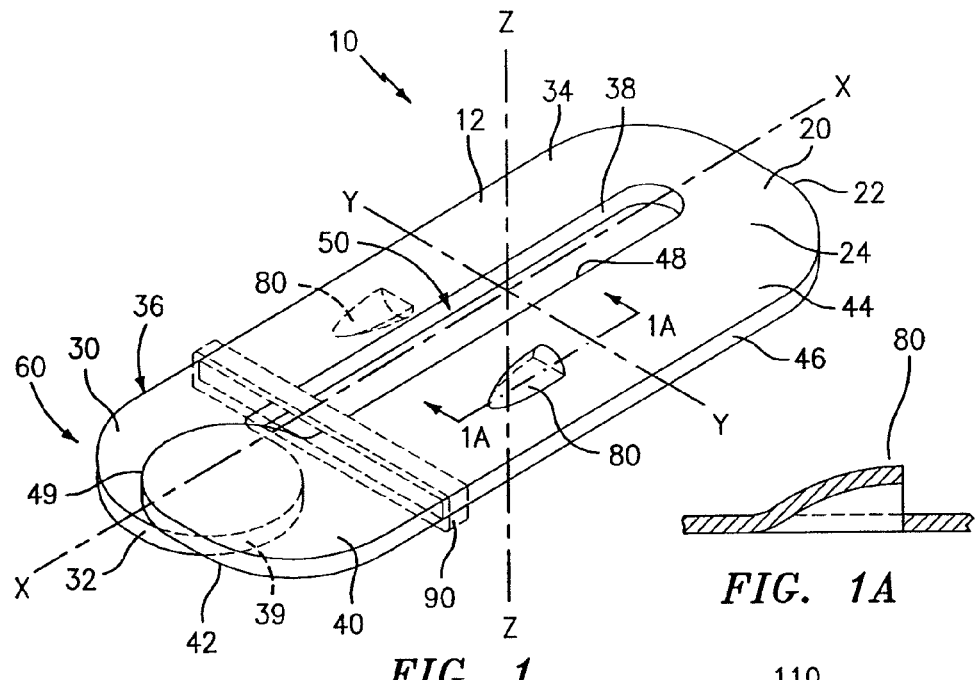
FIG. 1
FIG. 1A
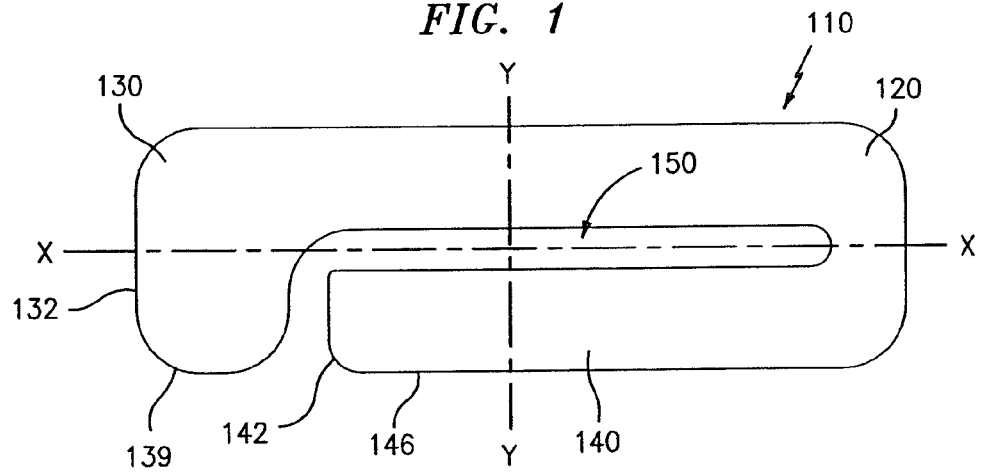
FIG. 2
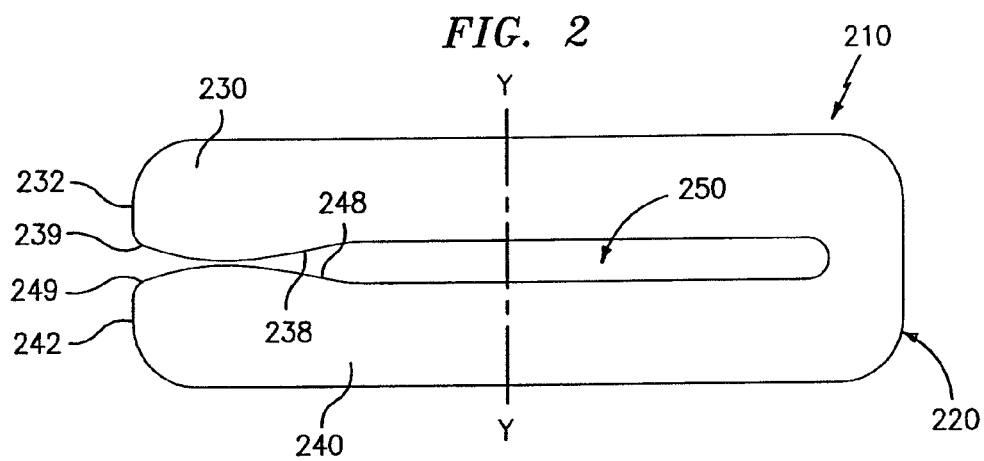
FIG. 3

ENDOSCOPIC SURGICAL CLIP

CROSS REFERENCE TO RELATED APPLICATIONS

This application is a Continuation of U.S. Ser. No. 10/421,151, filed Apr. 22, 2003 now U.S. Pat. No. 7,896,896, which claims priority from and the benefits of U.S. Provisional Application Ser. No. 60/374,623, filed on Apr. 22, 2002, the entire contents of which are hereby incorporated by reference.

BACKGROUND

1. Technical Field

The present disclosure relates to devices and methods for occluding vessels. More particularly, the present disclosure relates to ligating clips and methods for using ligating clips during surgical procedures.

2. Background of Related Art

During surgical procedures, it is frequently required either to occlude vessels temporarily or permanently to prevent the leakage of blood through incisions made at a surgical site. A wide variety of surgical ligating device configurations and techniques exist for accomplishing temporary and permanent occlusions. These include, for example, tubular, rod, and wire devices typically biased to a closed position. Ligating clips are configured for application directly by the hand of a surgeon, by remotely operated devices in open surgery, and/or by specialized instruments for minimally invasive surgical procedures.

Ligating clips used in minimally invasive surgery are frequently constrained in their configuration by their requirement to feed in series into an instrument configured for remotely applying clips. The requirement for compatibility with the applying instrument can often constrain the configuration of the clip.

Many ligating clips are formed of ductile material, e.g. metal, which clips, once applied, are largely unresponsive to changes in vessel wall thickness, for example, due to swelling, inflammation, or shrinkage. Such clips in certain instances may traumatize the vessel wall or not maintain the desired occlusion force. Thus, a need exists for ligating spring, or surgical, clips that are more responsive to changes in vessel wall thickness, by the clip allowing for expansion or spreading of the occluding portions of the clip to accommodate vessel wall swelling or inflammation, or providing further closure of the clip to adjust for vessel wall shrinkage. There is a need for such ligating spring, or surgical, clips that can adjust to reduce traumatization and/or maintain sufficient occlusion force.

A need also exists for simplified ligating clips with simplified shapes that can be applied remotely by a hand-held instrument during minimally invasive surgical procedures.

SUMMARY

This invention is directed to a spring clip for occluding a vessel and including a base and a jaw. The jaw is in a substantially planar arrangement with the base and includes elongate first and second arms with front and tail ends. The tail ends of each are in flexible communication with the base to define a longitudinal axis where the arms are moveable in an axis perpendicular to the longitudinal axis. At least one arm can have a tab adjacent its front end. Alternatively, the front ends of the arms can each include a tab where the tabs overlap. The tabs may be arcuately shaped. The first arm can be in a substantially planar arrangement with the second arm along the longitudinal axis. The first arm may be spaced apart from the second arm where the arms define a slot therebetween. The front end of the first arm may include a tab that is disposed orthogonally to the first arm and in front of the second arm. The arms may be substantially equal in length. The first arm can be longer than the second arm. A retention mechanism can be disposed perpendicularly to the longitudinal axis to urge the first and second arms into a predetermined relationship. Each the arm may also include at least one socket for receiving a biasing mechanism where the biasing mechanism is capable of moving the arms in opposing directions away from the longitudinal axis.

This invention is further directed to a surgical spring clip for occluding a vessel that includes a rigid base having a back end portion and a jaw. The jaw is in a substantially planar arrangement with the base and includes first and second elongate arms that are disposed in a substantially planar arrangement to define a first, closed position of the clip. The arms are substantially parallel to each other defining a longitudinal axis and are spaced apart from each other defining a slot. The arms further have front and tail end portions where the front end portions flexibly extend from the base. The front end portion of at least one of the arms can include a tab. The at least one tab can have a protrusion that is oriented towards the slot. The at least one tab may extends beyond a centerline of the slot. The first arm can be substantially equal in length to the second arm. The first arm can be longer than the second arm and includes a tab oriented to transect an imaginary line extending from the centerline of the slot. The tail ends of the first and second arms can communicate with the back end portion of the base.

The presently disclosed endoscopic spring clip, together with attendant advantages, will be best understood by reference to the following detailed description in conjunction with the figures below.

BRIEF DESCRIPTION OF THE DRAWINGS

Preferred embodiments of the presently disclosed endoscopic surgical clip are described herein with reference to the drawings, wherein:

FIG. 1 is a perspective view of one embodiment of an endoscopic surgical clip in a first position in accordance with the present disclosure;

FIG. 1A is a vertical sectional view, with portions taken away, as would be seen along line A-A of FIG. 1;

FIG. 2 is a top view of a second embodiment of the endoscopic surgical clip in a first position in accordance with the present disclosure;

FIG. 3 is a top view of a third embodiment of the endoscopic surgical clip in a first position in accordance with the present disclosure;

DETAILED DESCRIPTION OF PREFERRED EMBODIMENTS

Figure 4:
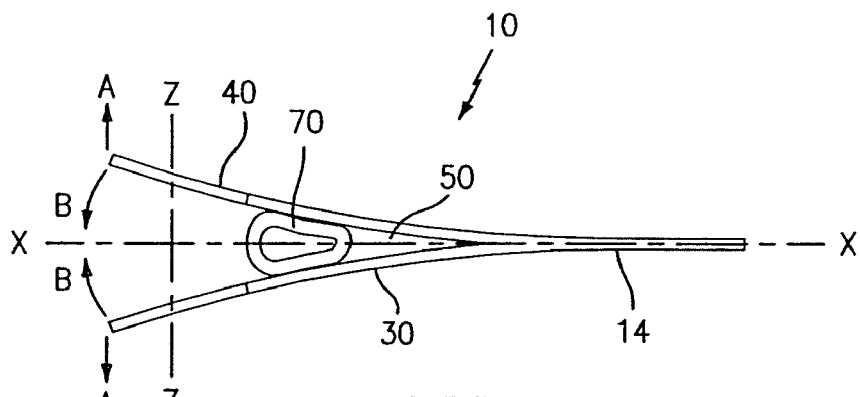
FIG. 4 is a side view of the endoscopic surgical clip of FIG. 1 in a second position with a vessel generally aligned with the axis-Y and positioned between the arms.
Figure 5:
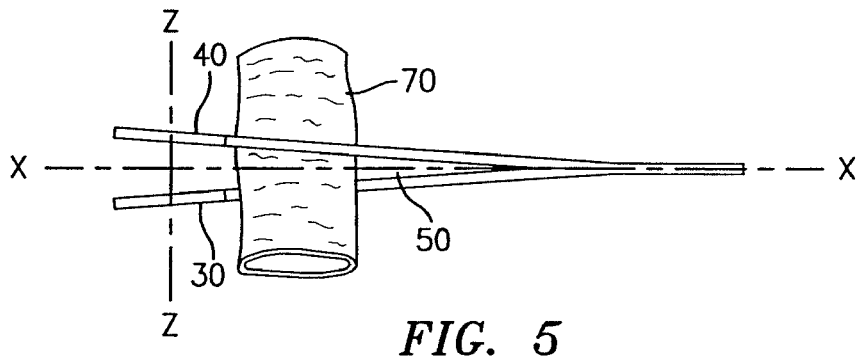
FIG. 5 is the side view of the endoscopic surgical clip of FIG. 4 in transition from the second position towards the first position with the vessel positioned between the arms and moving relative to the clip between the axes Y and Z.
Figures 6, 7:
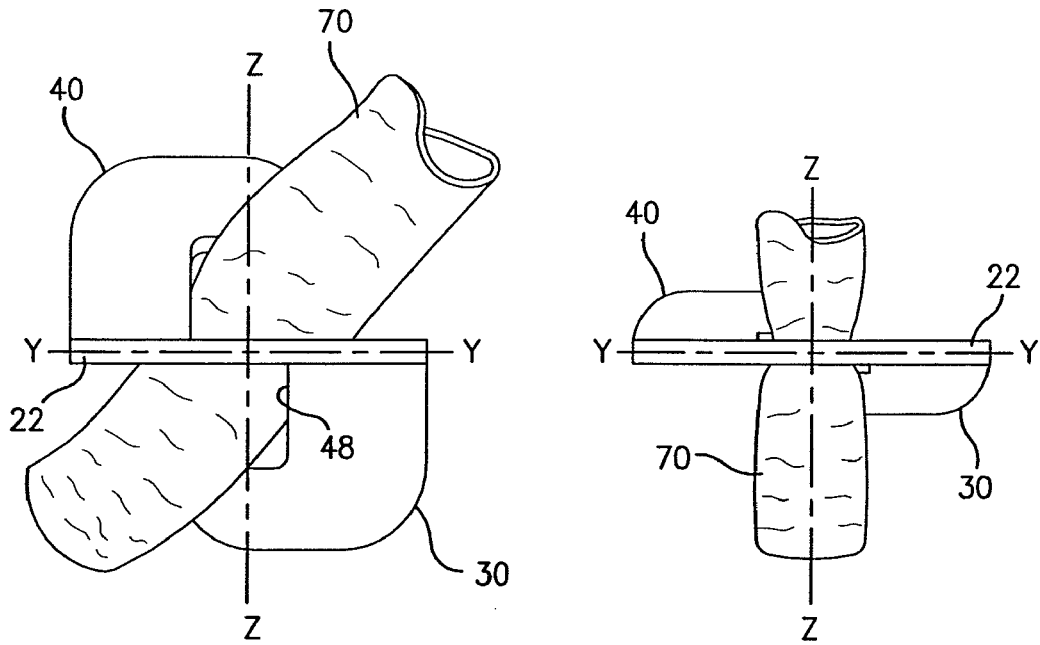
FIG. 6 is an base end view, with portions removed, of the base and arms of endoscopic surgical clip of FIG. 4 in transition from the second position towards the first position with the vessel positioned between the arms and in transition relative to the clip between the axes Y and Z.
FIG. 7 is a base end view, with portions removed, of the base and arms of the endoscopic surgical clip of FIG. 5 approximately in the first position with the ligating surgical clip generally aligned with the plane X-Y and the vessel generally aligned with axis-Z.

Referring now in specific detail to the drawings in which like referenced numerals identify similar or identical elements throughout the several views, and initially to FIGS. 1, 4, and 6, a surgical spring clip or a ligating clip 10, preferably an endoscopic spring clip, constructed in accordance with the present disclosure, is shown in a first, closed, position. Ligating clip 10 includes a preferably rigid base 20 and a jaw 60. Jaw 60 includes a first arm 30 and a second arm 40. Ligating clip 10 has an elongate plate-like shape defining a longitudinal axis-X and having a first face 12 and an opposed second face 14 (not shown) oriented in opposing directions of an axis-Z. Arms 30 and 40 are cantilevered elements extending from base 20 and are generally parallel with a longitudinal axis-X. An axis-Y intersects and is perpendicular to longitudinal axis-X and arms 30 and 40. Axis-Z intersects with and is perpendicular to axes X and Y.

Base 20 has a back end 22 and a back end portion 24. Base 20 connects or is in flexible communication with arms 30 and 40 and is configured to support the flexing of arms 30 and 40 along axis-Z. Alternative back end 22 or base 20 configurations include a tube or rod forming an axle parallel with axis-Y connecting two separate arms 30 and 40 together and providing suitable bias and structural integrity. It is also contemplated that the base 20 may be thicker or thinner in dimension relative to arms 30 and 40 in the direction of axis-Z.

Arms 30 and 40 each have front end portions or tips 32 and 42 respectively and tail ends 34 and 44 connected to base 20. Arm 30 has an outer edge 36 and an inner edge 38. Arm 40 similarly has an outer edge 46 and an inner edge 48. Inner edges 38 and 48 of tips 32 and 42 preferably have arcuately shaped and inwardly projecting tabs 39 and 49, respectively, generally parallel with axis-Y. Tab 39 of tip 32 and tab 49 of tip 42 preferably are at least partially overlapping in the direction of axis-Z and are configured to be biased by base 20 to the first or closed position wherein upper face 12 of tab 39 is in direct contact with lower face 14 (not shown) of tab 49. Tabs 39 and 49 function to limit the travel of the adjacent arms and secure clip 10 in the first position. The configuration of ligation clip 10 accommodates either tab 49 positioned over tab 39 as shown in FIG. 1, or in the alternative, tab 39 positioned over tab 49. Arms 30, 40 may have a uniform thickness in the direction of axis-Z or have a tapered configuration such that the thickness in the direction of axis-Z can vary between tail ends 34 and 44, and front end portions or tips 32 and 42.

Edges 38 and 48 are shown as having faces generally parallel with axis-Z. Further still, edges 38 and 48 can include bevels or concave portions configured to spread the load of arms 30 and 40 over a greater applied surface area of a vessel and thereby reduce the trauma to the vessel. A slot 50 is defined by inner edges 38 and 48, tabs 39 and 49, and the edge partly defining base 20. Slot 50 separates, and is defined by, arms 30 and 40 and enables the independent relative movement of arms 30 and 40 along axis-Z. The plate-like shape of arms 30, 40 inhibit movement of arms 30, 40 along axis-Y. Slot 50 is shown in this one preferred embodiment as an elongate slot generally parallel with the longitudinal axis-X. Tabs 39 and 39 define a front end of slot 50. Edges 38 and 48 defining slot 50 can include undulations, patterns, cut out portions and/or surface finishes to improve the positioning, grip, or retention of ligating clip 10 at a desired point on a vessel 70. Alternatively, edges 38 and 48 can include lubrication positioned on the surface or embedded within the material of edges 38 and 48.

Arms 30 and 40 flex about the vicinity of the junction of tail ends 34 and 44 with base 20 in the general direction of axis-Z from the biased, closed, first position to a second, or open, position. Base 20 provides sufficient structural integrity to inhibit the bending of base 20. In the first, or closed, position, arms 30 and 40 as well as base 20 are generally in alignment with each other and in a plane defined by axes X-Y. This would be equally true if arms 30, 40 did not have overlapping tabs 39, 39. Tips 32 and 42 are biased to be in direct contact and may extend out from plane X-Y. In the second, or open, position, at least one of arms 30 and 40 has moved to diverge from plane X-Y in one of the directions along axis-Z and arms 30 and 40 may have taken on an arcuate or straight configuration. Arms 30 and 40 in the second or open position define a range of channels between axes Y and Z suitable for the passage of vessel 70 therethrough and into, or within, slot 50. Arms 30 and 40 are configured to resist and preclude flexing or bending in the general direction of axis-Y.

In a preferred embodiment, arms 30 and 40 have a generally rigid or semi-rigid construction and are configured to resist, for example, torquing forces about axes parallel with axis-X and forces generally aligned with axis-Y. In the alternative, arms 30 and 40 can have a construction such that arms 30 and 40 can flex at multiple or infinite points about axes parallel to axis Y and still retain sufficient rigidity and strength in the general directions of axis-Y to constrict a vessel positioned within slot 50. Arms 30 and 40 can be sufficiently rigid such that tabs 39 and 49 directly intersect and block the passage of arms 30 and 40 past one another in the opposing directions of axis-Z. In the alternative, arms 30 and 40 can have sufficient flexibility to accommodate the rotation of arms 30 and 40 and/or flexing of tabs 39 and 49 sufficiently for arms 30 and 40 to pass by one another in the direction of axis-Z when external forces are applied in the direction of axis-Z.

Ligating clip 10 in any embodiment can include a retention mechanism 90 (shown in FIG. 1 in dashed lines) disposed perpendicularly to axis-X and configured to urge arms 30, 40 and position tips 32 and 42 in a secure predetermined relationship. Retention mechanism 90 can include known mechanical banding mechanisms, such as an elastic strap configured for accommodating the opposing tab 39 or 49, as well as a band configured to apply a bias along axes Y and/or Z to retain tabs 39 and 49 together. Tabs 39 and 49 can include interlocking edges with mating or interlocking cutouts to assist in retaining arms 30 and 40 in the first position. Further, slot 50 can be configured to define multiple stair-stepped channels and interlocking positions to accommodate two or more cross-sectional sizes of vessels within the length of slot 50 by varying the distances between edges 38 and 48. By varying the width of the slot 50 in the direction of the axis-Y, the amount of pressure applied to a given vessel can be selectively controlled.

Ligating clips 10 can also include mechanical assistance devices or features to assist in biasing or spreading arms 30, 40 to facilitate the application of ligating clips 10 to vessels 70 during minimally invasive surgery. For example, a pair of sockets 80 extending in directions along axis-Z can be provided in upper face 12 and lower face 14, to receive elongated members, e.g. pins that would facilitate opening arms 30, 40. Alternatively, a pair of sockets 80 could be defined as holes, and could be disposed, for example, parallel to axis-X through back end 22 of base 20 and extending distally at least partially within arms 30 and 40. Sockets 80 could also be at least one slot formed, for example, in edges 36 and 46 for the manipulation of arms 30 and 40 in opposite directions from axis-X, respectively. Thus, sockets 80 can provide an additional method for remotely spreading arms 30 and 40 in opposing directions of axis-Z for the positioning of a vessel during endoscopic or minimally invasive surgery.

Ligating clip 10 can be fabricated of a suitable medical grade metal, composite, or plastic material providing a flexing or spring type pivotal movement and a bias to arms 30 and 40 as well as sufficient rigidity for securely clipping a vessel in the first position. Ligating clip 10 can have a uniform composition, different base and arm materials, or have a laminated structure of varying composition.

Referring now to FIG. 2, ligating clip 110 in a second preferred embodiment has a base 120, first arm 130, and second arm 140. Ligating clip 110 has a flat planar construction aligned with a plane defined by the intersection of orthogonal longitudinal axis-X and axis-Y. First arm 130 has a greater length along axis-X than second arm 140. Arm 130 has a tip 132 having a tab 139 with a 90° or right angle bend extending perpendicular to axis-X and in the direction of axis-Y until it is approximately in front of and aligned with an outer edge 146. Arm 140 has a straight elongate shape terminating in a tip 142. An open-ended slot 50 is defined by base 120, arm 130, and arm 140. Slot 50 extends along axis-X from base 120 and makes a right angle bend between tip 142 and tab 139.

FIG. 3 shows a third embodiment of a ligating clip, generally designated 210, having a base 220, first arm 230, and second arm 240. Ligating clip 210 has a flat planar construction aligned with a plane defined by the intersection of orthogonal longitudinal axis-X and axis-Y. First arm 230 and second arm 240 have an approximately equal length along axis-X and include tips 232 and 342 having inwardly projecting tabs 239 and 249. Tabs 239 and 249 have an opposing orientation and are parallel with axis-Y. A slot 250, aligned with longitudinal axis-X, is defined by inside edges 238 and 248. Edge 238 of tab 239 and edge 248 of tab 249 can be configured to be adjacent to each other, as shown, and defining an opened ended slot 250, or in direct contact, terminating slot 250. Tabs 239 and 249 may be configured to provide a mating interface such as a tongue and groove for forming a friction based connection at tips 232 and 242.

In operation, spring or flexible ligating clips 10, 110, and 210 (for simplicity, hereinafter, 10) are preferably applied during minimally invasive surgical procedures. Ligating clip 10 has a first position, as shown in FIG. 1, with tabs 39 and 49 of tips 32 and 42, respectively, being in an overlapped position. Arms 30 and 40 are preferably biased to the first, or closed, position and generally positioned within the plane defined by axes X and Y.

Ligating clip 10 in the second position, as shown in FIGS. 4 and 6, has arms 30 and 40 flexing in opposing directions along axis-Z as a result of a force or forces effectively applied in the general direction of axis-Z. Arms 30 and 40, separated along axis-Z in a second, or open, position create a range of channels between axis-Y and axis-Z. Jaw 60 is in an open or spread position against the bias of forces-B as applied by base 20 on arms 30 and 40 urging jaws 60 to the first position.

Referring now to FIGS. 4-7, ligating clip 10 is shown in this one preferred embodiment having vessel 70 initially positioned in approximate alignment with axis-Y between arms 30 and 40 in the second position. Upon the removal of forces-A, the bias in ligating clip 10 is shown as forces-B in the opposing direction of axis-Z, drives arms 30 and 40 to return to the first position. Ligating clip 10 is shown in steps returning to the first position from the second position as the relative positional relationship between vessel 70 and ligating clip 10 (FIG. 4) transitions from the vessel being approximately aligned with axis-Y to being approximately aligned with axis-Z (FIG. 7). The scissor type action of arms 30 and 40 in the first position securely constricts, or occludes, vessel 70 from fluid communication. Depending on the circumstances, ligating clip 10 can be left permanently in position or subsequently removed if it is temporarily applied.

Although it is envisioned that the width of slots 50, 150, or 250 of ligating clips 10, 110, or 210 theoretically can be the same or less than the same dimensions as the total thickness of the particular vessel(s) to be occluded, the actual width(s) of slots 50, 150, or 250 will depend upon various factors, including the thickness and condition of the vessels to be occluded, and can be determined from experimental data that will render the desired dimension apparent to those skilled in the art.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed:

1. A surgical spring clip for occluding a vessel, comprising:
a rigid substantially planar base;
a jaw in a substantially planar arrangement with the base and including first and second elongate arms, the first and second arms being disposed in a substantially coplanar arrangement in a first, closed position of the clip, the arms being substantially parallel to and spaced apart from each other, the arms defining a longitudinal plane extending therebetween and defining a slot having a width less than a width of either the first or second arms, the arms further having front and tail ends, the front ends flexibly extending perpendicular from the base from the first closed position to a vertically spaced apart second position; and
a tab disposed on the front end of each of the first and second elongate arms wherein at least a portion of each of the tabs extends through a longitudinal plane bisecting the slot and are in contact with each other when the front ends are in the first, closed position and at least a portion of each tab extends through the longitudinal plane bisecting the slot and are vertically spaced apart and at least a portion of each tab extends through the longitudinal plane bisecting the slot when the front ends are in the second position.

2. The clip of claim 1, wherein at least one of the tabs forms a distal end of the slot.

3. The clip of claim 1, wherein at least one tab is oriented towards the slot.

4. The clip of claim 3, wherein the at least one tab extends beyond a centerline of the slot.

5. The clip of claim 1, wherein the first arm is substantially equal in length to the second arm.

6. The clip of claim 4, wherein the first arm is longer than the second arm and includes a tab oriented to transect an imaginary line extending from the centerline of the slot.

7. The clip of claim 1, wherein a bottom face of the tab disposed on the first elongate arm is in contact with a top face of the tab disposed on the second elongate arm.

8. The clip of claim 1, wherein the tabs are vertically positioned along a vertical axis in both the first and second positions.

9. The clip of claim 1, wherein each tab extends beyond a centerline of the slot.

10. A surgical spring clip for occluding a vessel, comprising:
   a rigid planar base;
   a jaw including first and second elongate arms, the arms being substantially parallel to each other in a substantially planar arrangement, wherein the arms are spaced apart from each other and define an elongated slot therebetween, the slot having a width less than a width of either the first or second arms; and
   a pair of tabs disposed on the front end of each of the first and second elongate arms, wherein at least a portion of each of the tabs extends beyond the width of the slot when the arms are in a first, closed position and when the arms are in a second open, vertically spaced apart, position for the reception of a vessel therebetween.

11. The clip of claim 10, wherein a bottom face of the tab disposed on the first elongate arm is in contact with a top face of the tab disposed on the second elongate arm.

12. The clip of claim 10, wherein the tab is vertically positioned along a vertical axis in both the first and second positions.

13. A surgical spring clip for occluding a vessel, comprising:
   a rigid planar base;
   a jaw including first and second elongate arms, the arms being substantially parallel to each other in a substantially planar arrangement, wherein the first arm is substantially equal in length to the second arm and the arms are spaced apart from each other to define an elongated slot therebetween, the slot having a width less than a width of either the first or second arms; and
   a tab disposed on the front end of at least one of the first and second elongate arms wherein at least a portion of the tab extends beyond the width of the slot when the arms are in a first, closed position and when the arms are in a second open, vertically spaced apart, position for the reception of a vessel therebetween.

14. The clip of claim 13, wherein the tab is vertically positioned along a vertical axis in both the first and second positions.

* * * * *